United States Patent
Wong

(10) Patent No.: US 11,523,794 B2
(45) Date of Patent: Dec. 13, 2022

(54) QUICK RELEASE STRUCTURE OF DIAPHRAGM ASSEMBLY OF STETHOSCOPE

(71) Applicant: CHIN KOU MEDICAL INSTRUMENT CO., LTD., New Taipei (TW)

(72) Inventor: Chung-Jen Wong, New Taipei (TW)

(73) Assignee: CHIN KOU MEDICAL INSTRUMENT CO., LTD., New Taipei (TW)

( * ) Notice: Subject to any disclaimer, the term of this patent is extended or adjusted under 35 U.S.C. 154(b) by 79 days.

(21) Appl. No.: 17/226,041

(22) Filed: Apr. 8, 2021

(65) Prior Publication Data

US 2022/0323042 A1 Oct. 13, 2022

(51) Int. Cl.
*A61B 7/02* (2006.01)

(52) U.S. Cl.
CPC ..................... *A61B 7/02* (2013.01)

(58) Field of Classification Search
CPC ....................................... A61B 7/02
See application file for complete search history.

(56) References Cited

U.S. PATENT DOCUMENTS

| | | | |
|---|---|---|---|
| 4,440,258 A * | 4/1984 | Packard | A61B 7/02 181/137 |
| 5,428,193 A | 6/1995 | Mandiberg | |
| 5,945,640 A * | 8/1999 | Rossini | A61B 7/026 181/131 |
| 6,019,187 A * | 2/2000 | Appavu | A61B 7/02 181/131 |
| 6,378,648 B1 * | 4/2002 | Werblud | A61B 7/02 181/131 |
| 6,520,281 B1 * | 2/2003 | Deslauriers | A61B 7/02 600/528 |
| 7,424,929 B1 | 9/2008 | Martinez | |
| 7,757,807 B1 | 7/2010 | Martinez | |
| 8,051,946 B1 | 11/2011 | Murad | |
| 9,770,307 B2 | 9/2017 | Krupnick | |

(Continued)

FOREIGN PATENT DOCUMENTS

| | | | | |
|---|---|---|---|---|
| CN | 103315768 A | * | 9/2013 | ............... A61B 7/02 |
| EP | 2389010 A1 | * | 11/2011 | ............... A61B 7/02 |
| TW | M606847 U | * | 1/2021 | |

*Primary Examiner* — Jeremy A Luks
(74) *Attorney, Agent, or Firm* — Keong C. Lei

(57) ABSTRACT

A quick release structure of a diaphragm assembly of a stethoscope is disclosed, including a stethoscope having two collecting surfaces each being connectable with a diaphragm assembly. The collecting surface has a portion adjacent to an outer periphery thereof and formed with an annular fitting groove that has a height lower than the collecting surface. The collecting surface is formed with a trough. The annular fitting groove has an inclined internal wall. The diaphragm assembly includes an elastic piece combined with a diaphragm assembly. The elastic piece includes a raised rib, a projection portion, and an inclined inside surface. Through pressing the raised rib into the annular fitting groove, the inside surface is set in tight engagement with the internal wall, and this, in combination with the projection portion fit in the trough, forms a secure and stable fitting engagement and allowing easy release performed in an opposite way.

2 Claims, 8 Drawing Sheets

(56) References Cited

U.S. PATENT DOCUMENTS

2005/0257996 A1* 11/2005 Brown ................. A61B 7/02
  181/131
2009/0211838 A1    8/2009 Bilan
2018/0214114 A1    8/2018 Keller
2018/0344282 A1* 12/2018 Lin ..................... A61B 7/02
2021/0369233 A1* 12/2021 Kays ................... B22F 3/1021

* cited by examiner

QUICK RELEASE STRUCTURE OF DIAPHRAGM ASSEMBLY OF STETHOSCOPE

TECHNICAL FIELD OF THE INVENTION

The present invention relates to the field of stethoscopes, and more particularly to a quick release structure of a diaphragm assembly of a stethoscope.

DESCRIPTION OF THE PRIOR ART

A known stethoscope comprises a diaphragm that is of a multiple-piece structure made up of a rim and a piece of diaphragm. Each time when it needs to replace a new piece of diaphragm, the rim and the diaphragm must be carefully and tightly fit together for gap sealing. Once the replacement is performed frequently, the rim may get elastically relaxed, making it not possible to achieve effect sealing.

One-piece diaphragm products have been later proposed and available. For example, U.S. Pat. No. 10,213,181 B2 provides a stethoscope diaphragm, which effectively surmounts inconvenience of carefully checking whether sealing has been done in replacement and also overcomes hygiene issues of repeated use.

The improved product as discussed above improves the shortcomings of the early-day stethoscopes. Nevertheless, such a product stiff suffers certain drawbacks to be further improved. A drawback is that since the structural feature of the combination of the one-piece diaphragm and the stethoscope body is such that contraction of an elastic material along an edge of the diaphragm is used for positioning with respect to a recess provided in the stethoscope body in a fitting and fixed condition, to replace, the diaphragm is hard to release and remove, making the operation time of diaphragm replacement extended for quite an amount.

SUMMARY OF THE INVENTION

The primary objective of the present invention is to provide a quick release structure of a diaphragm assembly of a stethoscope, wherein a stethoscope head has two collection surfaces, each of which is connectable with an integrally-formed one-piece diaphragm assembly made up of an elastic piece and a diaphragm, providing the diaphragm assembly with advantages of stable connection and easy release.

The technical solution that the present invention adopts to overcome the technical issues has a main structure that comprises a stethoscope head having two collecting surfaces to be connectable with a diaphragm assembly, wherein each of the collecting surfaces has a portion adjacent to an outer periphery thereof and formed, through recessing, with an annular fitting groove. The annular fitting groove has a height lower than the collecting surface. Each of the collecting surfaces is formed with a trough. The diaphragm assembly is formed of an elastic piece having an inner circumference combined with a diaphragm. The elastic piece is provided with a raised rib and a projection portion. The raised rib is set corresponding to the annular fitting groove and is subject to pressing to fit into and embed in the through in a manner of being in collaboration with the projection portion so as to form a secure and stable fitting connection.

The secondary technical purpose is that the annular fitting groove is provided with an internal wall, and the internal wall is provided in the annular fitting groove, and the internal wall has an inclined structure having a top wide and bottom narrow arrangement.

The tertiary technical purpose is that the raised rib has an inside surface that is of an inclined surface structure having a top narrow and bottom wide arrangement to provide a primary function of being set in tight engagement with the internal wall.

The quaternary technical purpose is that the diaphragm assembly is alterable to an arrangement that includes an elastic piece but has no diaphragm and is usable with the elastic piece having the diaphragm.

The quinary technical purpose is that the elastic piece is further provided with an extension portion, which is provided on an outer circumferential edge of the elastic piece to be gripped and nipped by a user's hand in order to enhance convenience of removing and replacing the diaphragm assembly.

Based on the above novel and unique design, the present invention, when compared with the prior art, allows an annular fitting groove formed, through recessing, in a portion of the collecting surface of the stethoscope head that is adjacent to an outer periphery thereof and a trough formed in the collecting surface to connect with a diaphragm assembly that is made up of an elastic piece and a diaphragm, so as to provide a quick release structure for the diaphragm assembly of the stethoscope to thereby alleviate inconvenience of releasing and assembling and also providing stability for not easily detaching.

DETAILED DESCRIPTION OF THE PREFERRED EMBODIMENT

Figure 1:
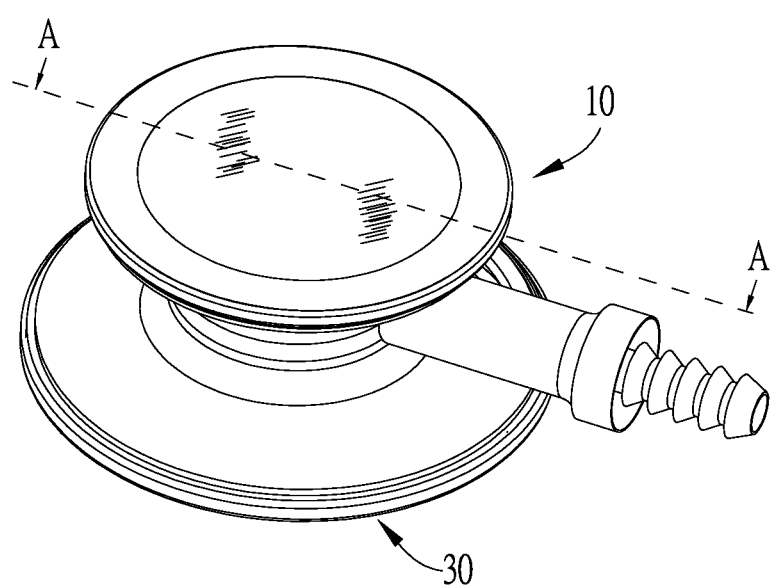
FIG. 1 is a perspective view of the present invention.
Figure 2:
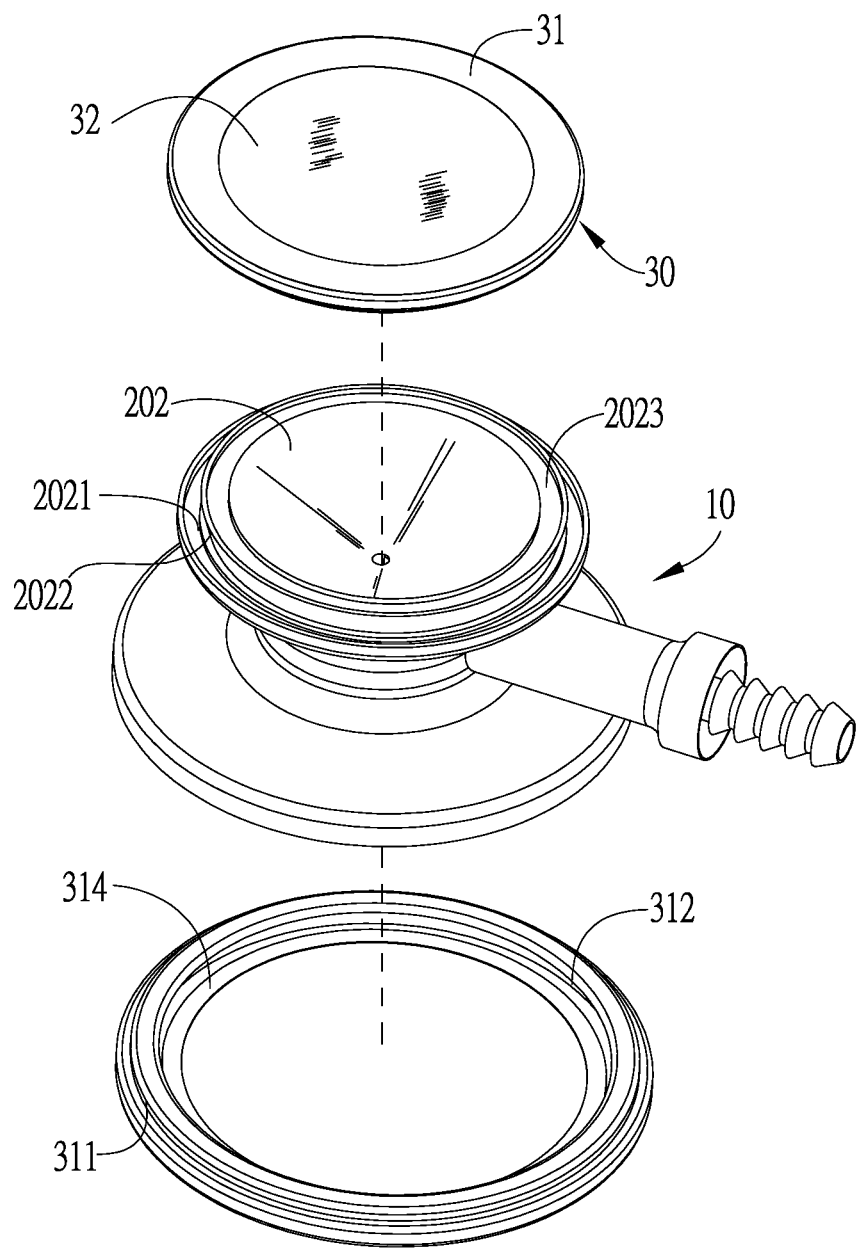
FIG. 2 is an exploded view of the present invention.
Figure 3:
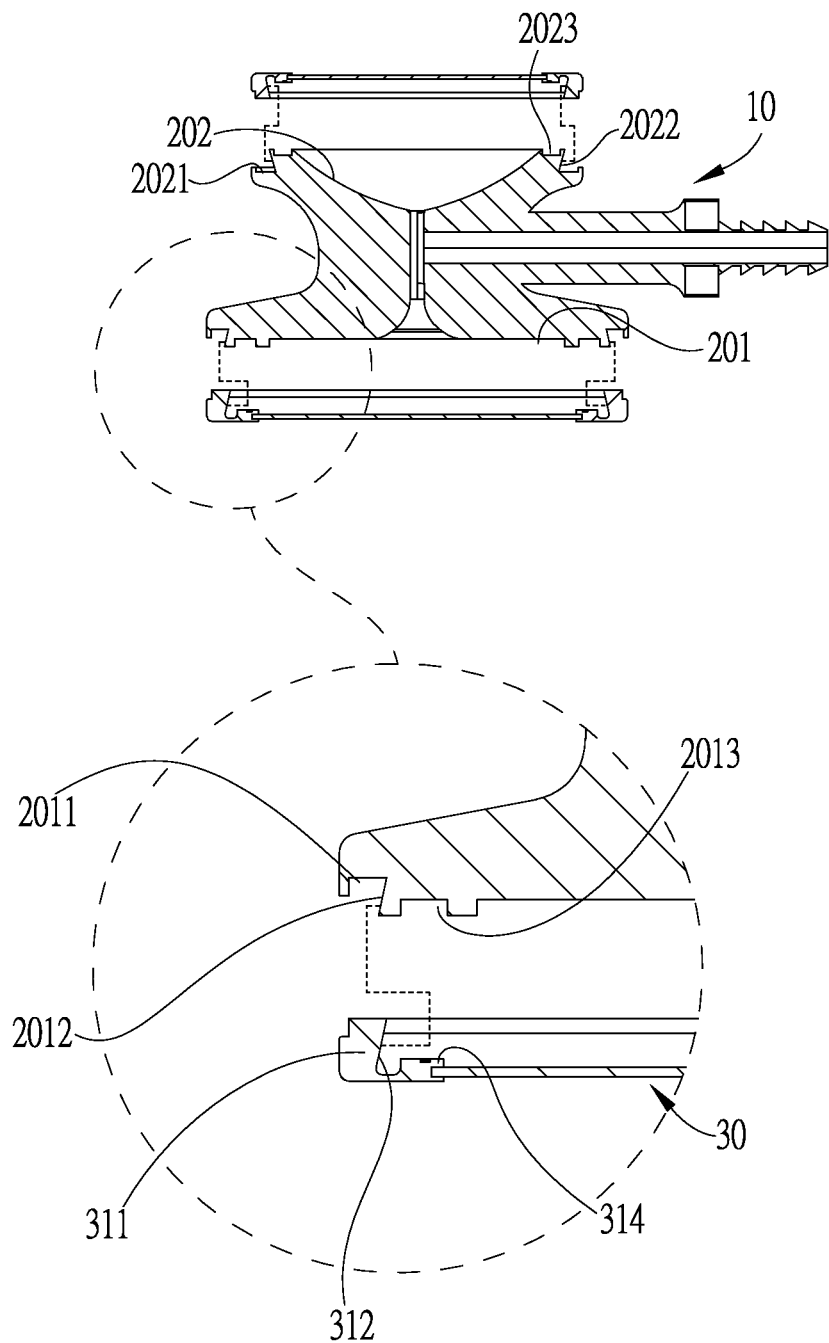
FIG. 3 is a cross-sectional view taken along line A-A of FIG. 1, of which a portion is enlarged to show one of a series of operations of connecting a diaphragm assembly to a stethoscope head according to the present invention.
Figure 4:
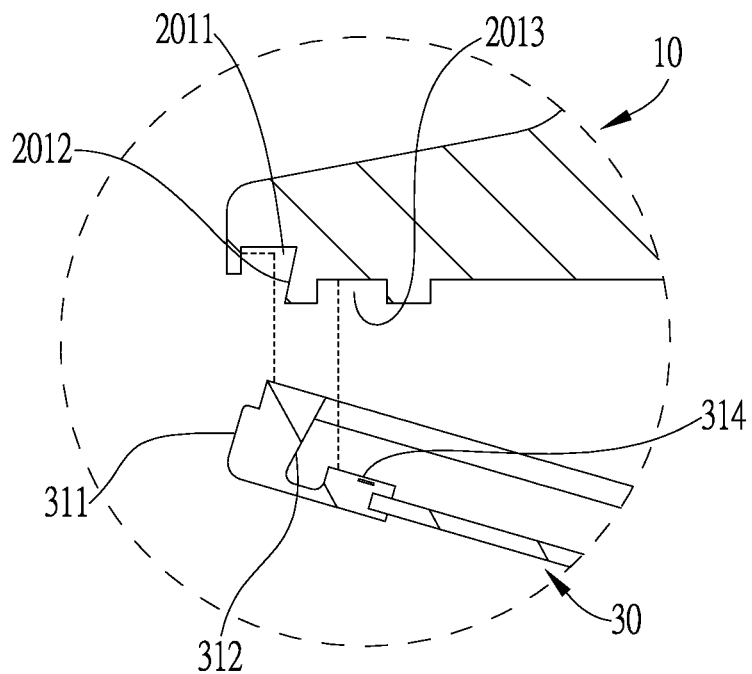
FIG. 4 is an enlarged view showing one of the series of operations of connecting the diaphragm assembly to the stethoscope head according to the present invention subsequent to FIG. 3.
Figure 5:
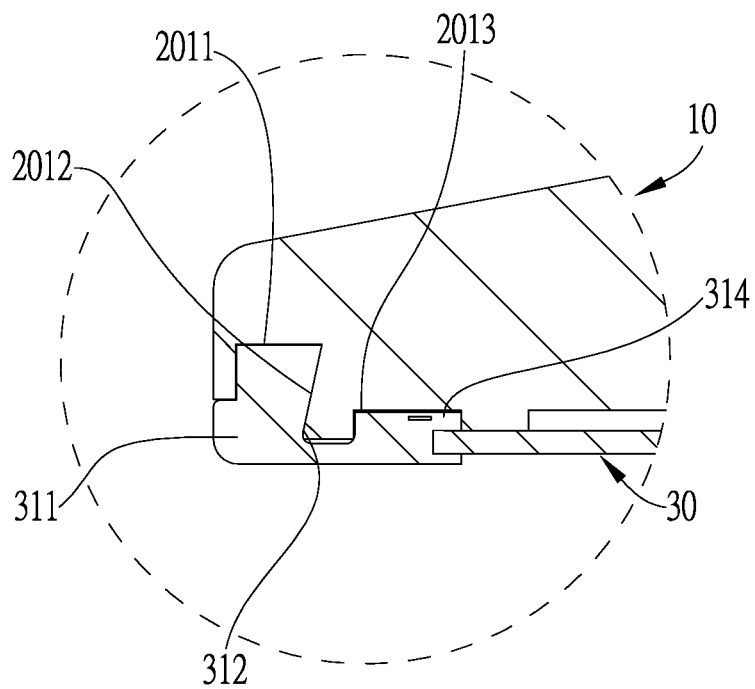
FIG. 5 is an enlarged view showing one of the series of operations of connecting the diaphragm assembly to the stethoscope head according to the present invention subsequent to FIG. 4.
Figure 6:
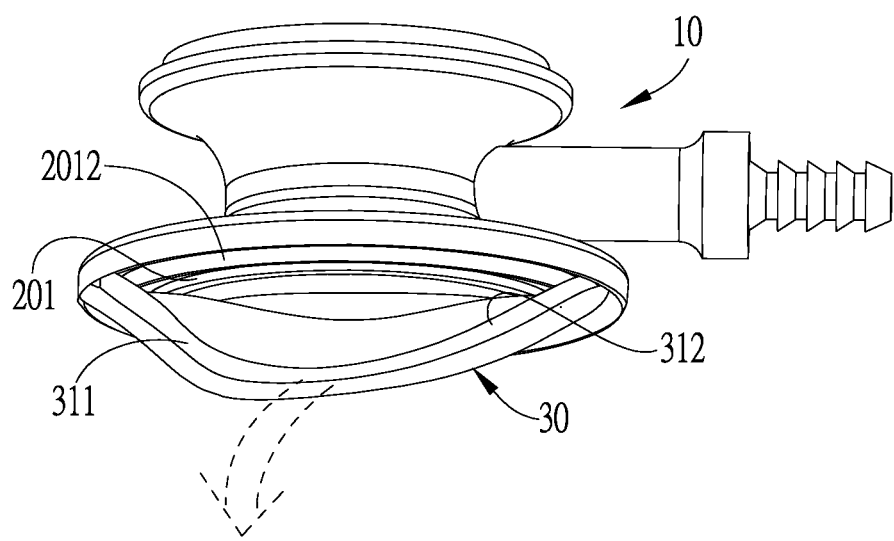
FIG. 6 is a schematic view showing the diaphragm assembly released from a collecting surface of the stethoscope head according to the present invention.

Generally according to the present invention, particularly, the best feasible embodiment, together with FIGS. 1-9, a detailed description will be provided to enhance understanding of the present invention. The present invention relates to a quick release structure that is used with a diaphragm assembly of a stethoscope. In the embodiment of the present invention, a dual-purpose stethoscope will be described, which comprises: a stethoscope head (10), which comprises two collecting surfaces (201, 202). Specifically, the collecting surfaces (201, 202) are classified as a large one and a small one. The large collecting surface is referred to as a first collecting surface (201), while the small collecting surface is referred to as a second collecting surface (202), wherein they are primarily different from each other for being respectively applicable to an adult and a child, and transmission of high frequency sounds and low frequency sounds, otherwise they have the same structure. Thus, in the following, only one of the surfaces will be described. The two collecting surfaces (201, 202) have a primary function of allowing each one to connect with a diaphragm assembly (30). The collecting surface (201, 202) has an outer peripheral edge and a portion adjacent thereto is formed, as being recessed, with an annular fitting groove (2011, 2021). The annular fitting groove (2011, 2021) has a height lower than the collecting surface (201, 202), meaning the first collecting surface (201) is higher, in height, than the annular fitting groove (2011), and the second collecting surface (202) is higher, in height, than the annular fitting groove (2021). Further, the collecting surface (201, 202) is formed with a trough (2013, 2023). The diaphragm assembly (30) is generally formed of an elastic piece (31), which is combined, along an inner circumference thereof, with a diaphragm (32). The elastic piece (31) is formed with a raised rib (311) and a projection portion (314). The raised rib (311) is set to correspond to the annular fitting groove (2011, 2021) and is pressed to fit into and embedded in the trough (2013, 2023) in a manner of being in collaboration with the projection portion (314), so as to provide a secure and stable connection through fitting engagement.

Referring to FIGS. 3-6, the annular fitting groove (2011, 2021) has an internal space that has an internal wall (2012, 2022) provided in the annular fitting groove (2011, 2021). The internal wall (2012, 2022) has an inclined structure having a wide top and narrow bottom arrangement. The annular fitting groove (2011) and the internal wall (2012) provided on the first collecting surface (201) allows a user to insert the raised rib (311) of the elastic piece (31) of the diaphragm assembly (30) into the annular fitting groove (2011) to make a mutually-interleaved stable connection state between the internal wall (2012) and the inside surface (312), and the projection portion (314) is fit into and embedded in the trough (2013). As such, assembling performance is increased and better stability is achieved. To replace a new diaphragm assembly (30), since the inside surface (312) of the raised rib (311) is also of an inclined structure having a top narrow and bottom wide arrangement, so as to present a tight fitting engagement with the internal wall (2012) and also to allow release to be easily performed in an opposite way by simply directly gripping and nipping and compressing the elastic piece (31) of the diaphragm assembly (30) with a hand to achieve direct removal for replacement with the new one, making the use easier and more convenient. The second collecting surface (202) is similarly provided with an annular fitting groove (2021), and the annular fitting groove (2021) is also of an inclined structure having a top wide and bottom narrow arrangement, so that such a structural arrangement, as well as use thereof, is similar to that of the first collecting surface (201) described above, and repeated description will be omitted herein.

Figure 7:
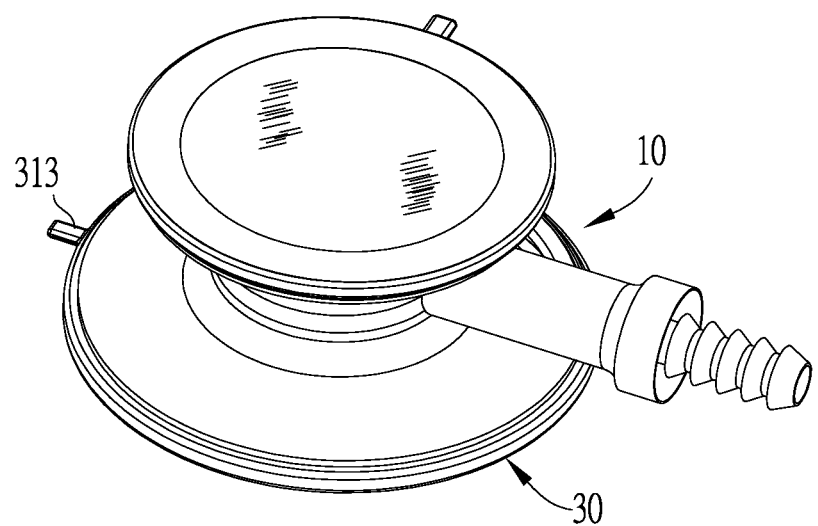
FIG. 7 is a perspective view showing another embodiment of the present invention.
Figure 8:
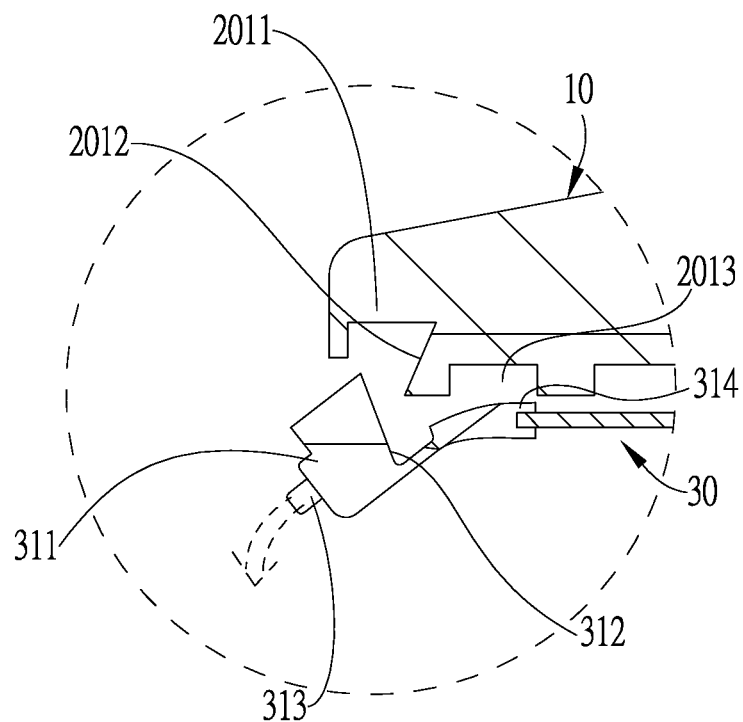
FIG. 8 is a schematic view showing an operation in respect of an extension portion of the present invention as shown in FIG. 7.

Referring to FIGS. 7 and 8, the elastic piece (31) has an outer circumferential edge that is formed with an extension portion (313). The extension portion (313) is provided on the outer circumferential edge to enable positional adjustment so as to reduce perception of contacting a foreign object when a user is using the stethoscope head (10), and providing a primary function of providing an increased contact area for a user's hand when being nipped by the user's hand, allowing easy application of a force by the user to release the elastic piece (31) from a state of being connected with the stethoscope head (10) to thereby further improve the convenience and efficiency of removing and replacing the diaphragm assembly (30). Further, the extension portion (313) can be made in different shapes and sizes as desired in order to accommodate the force applied from different user's hands that might be of different sizes, and no specific limitation is required in this invention.

Figure 9:
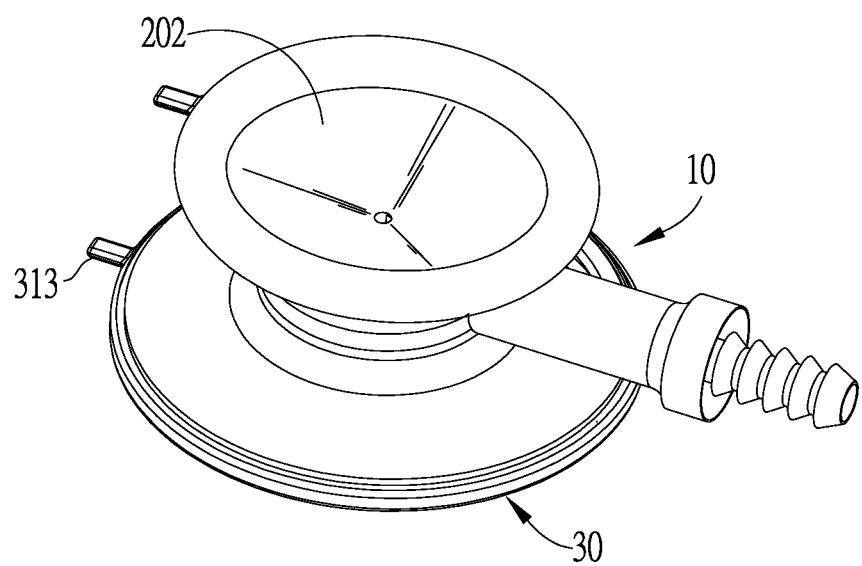
FIG. 9 is a schematic view showing an alternative embodiment of the diaphragm assembly according to the present invention.

Referring to FIG. 9, in an alternative arrangement, the diaphragm assembly (30) mounted to the second collecting surface (202) can be changed to an assembly that includes just an elastic piece (31) but no diaphragm at all, and is usable in combination with the elastic piece (31) of the first collecting surface (201) that is combined with a diaphragm (32), generally depending on the design purpose of the stethoscope head (10), and no limitation is imposed thereto.

In summary, the present invention provides a quick release structure for a diaphragm assembly of a stethoscope, which is generally structured such that each collecting surface (201, 202) is provided with an annular fitting groove (2011, 2021), and the annular fitting groove (2011, 2021) has an internal wall (2012, 2022) set in an inclination angle to allow an elastic piece (31) that is similarly provided with an inclined surface arrangement to combine therewith by means of a wide-narrow combined arrangement so as to achieve a secure and stable fitting engagement for the combination and also to allow release to be easily and conveniently performed in an opposite way.

I claim:

1. A quick release structure of a diaphragm assembly of a stethoscope, comprising: a stethoscope head, which comprises two collecting surfaces that are connectable with a diaphragm assembly, wherein the collecting surfaces have a portion that is adjacent to an outer periphery thereof and is formed, through recessing, with an annular fitting groove, such that the annular fitting groove has a height lower than the collecting surfaces, the collecting surfaces being further formed with a trough, the diaphragm assembly being formed of an elastic piece having an inner circumference combined with a diaphragm, the elastic piece being provided with a raised rib and a projection portion, wherein the raised rib is set corresponding to the annular fitting groove and is subject to pressing to fit into and embed in through in a manner of being in collaboration with the projection portion so as to form a secure and stable fitting connection; wherein the annular fitting groove further comprises an internal wall provided in the annular fitting groove, and the internal wall has an inclined structure having a top wide and bottom narrow arrangement; and wherein the raised rib comprises an inside surface that is of an inclined surface structure having a top narrow and bottom wide arrangement and enables tight engagement with the internal wall and allows easy release performed in an opposite way.

2. The quick release structure of the diaphragm assembly of the stethoscope according to claim 1, wherein the elastic piece further comprises an extension portion that is provided on an outer circumferential edge of the elastic piece and is adapted to be gripped and nipped by a user's hand in order to enhance convenience of removing and replacing the diaphragm assembly.

\* \* \* \* \*